US00PP12618P2

(12) United States Plant Patent
Walden

(10) Patent No.: US PP12,618 P2
(45) Date of Patent: May 7, 2002

(54) MINIATURE ROSE PLANT NAMED 'JACRENEW'

(75) Inventor: John K. Walden, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 09/400,728

(22) Filed: Sep. 21, 1999

(51) Int. Cl.[7] ..... A01H 5/00
(52) U.S. Cl. ..... Plt./122
(58) Field of Search ..... Plt./122, 116

*Primary Examiner*—Bruce R. Campell
*Assistant Examiner*—June Hwu
(74) *Attorney, Agent, or Firm*—Klarquist Sparkman, LLP

(57) ABSTRACT

A miniature rose plant having bright red, abundant flowers that darken in color as they age; dwarf, compact growth habit; dark green, glossy, abundant foliage; fast repeat bloom cycle; and resistance to powdery mildew.

1 Drawing Sheet

The present invention relates to a new and distinct variety of role plant of the miniature class which was originated by me by crossing an unpatented, unnamed seedling with the variety 'MACnewye,' U.S. Plant Pat. No. 5,428.

The primary objective of this breeding was to produce a new rose variety having stable, bright red, 2 to 2¼ inch flowers on a dwarf plant, having dark green, glossy, disease resistant foliage and free-flowering, an abundance of flowers through a fast repeat blooming cycle. The objective was substantially achieved, along with other desirable improvements, as evidenced by the following unique combination of characteristics that are outstanding in the new variety and that distinguish it from its parents, as well as from all other varieties of which I am aware:

1. Bright red, 2 to 2¼ inch flowers that darken with age maintaining a fresh appearance;
2. Dwarf, compact, round plant habit;
3. Abundant flower production and rapid repeat bloom cycle;
4. Dark green, glossy foliage; and
5. Resistance to powdery mildew.

COMPARISON WITH PARENTS

The female parent is a bright red miniature with ten petals, whereas JACrenew has 15–20 petals. The male parent, 'MACnewye' is a large flowered grandiflora rose having orange and gold blended flowers.

COMPARISON WITH SIMILAR VARIETY

JACrenim is a similar miniature but has small red flowers.

Asexual reproduction of this new variety by cuttings, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) colour chart, except where ordinary dictionary significance of color is indicated.

Parentage:

*Seed parent*.—Unnamed seedling (unnamed seedling× RUImired — (U.S. Plant Pat. No. 5,770).

*Pollen parent*.—'MACnewye' (U.S. Plant Pat. No. 5,428).

Classification:

*Botanical*—*Rosa Hybrida*.

*Commercial*.—Miniature rose.

FLOWER

Observations made in August 1999, from one-year old specimens grown in a garden environment at Somis, Calif.

Blooming habit: Recurrent.

Bud:

*Size*.—About ¾ to ⅞ inches long when the petals start to unfurl.

*Form*.—The bud form is short, pointed ovoid.

*Color*.—When sepals first divide, bud color is between Red Group 46A and Red Group 46B. When half blown, the upper and lower sides of the petals are near Red Group 45A.

*Sepals*.—Color: Between Yellow-Green Group 146B and Yellow-Green Group 146C, overlaid with Greyed-Purple Group 184A. Length: ¾–1 inch. Width: 3/16–¼ inch. Shape: Lancolate. Apex: Acuminate. Surface texture: Hairy and glandular There are three normally appendaged sepals. There are two unappendaged sepals with hairy edges.

*Receptacle*.—Color: Yellow-Green Group 144A. Shape: Funnel. Size: Small (about ¼ inch×5/16 inch). Surface: Smooth, hairy.

*Peduncle*.—Length: Medium (about 2⅜ inches). Surface: Slightly rough; glandular. Color: Yellow-Green Group 146B, and Greyed-Purple Group 184A where exposed to direct sunlight. Strength: Weak; bending.

Bloom:

*Size*.—Small. Average open size is 2 to 2½ inches.

*Borne*.—Singly and several together in flat clusters of three to seven blooms.

*Stems*.—Strength Normal. Average length is about six to eight inches.

*Form*: When first open: Cupped. Permanence: Retains its form to the end; petals curl back.

*Petalage*.—Number of petals under normal conditions: 15 to 20.

*Color*.—The upper sides of the petals are near Red Group 45A. The reverse sides of the petals are between Red Group 46A and Red Group 46B. The base of each petal has on both upper and reverse sides a 1/8 inch Yellow Group 6C crescent. The major color on the upper side is near Red Group 45A.

*Variegations*.—None.

*Discoloration*.—The general tonality at the end of the first day: Near Red Group 45A. At the end of the third day: Unchanged. With further aging, color is near Red Group 46A.

*Fragrance*.—None.

Petals:

*Texture*.—Thick, smooth and velvety.

*Shape*.—Deltoid. Base: Between cuneate and obtuse. Apex: Mucronate. Margin: Rounded and notched. Length: 3/4–1 inch. Width: 11/16–13/16 inch.

*Form*.—Tips slightly recurved.

*Arrangement*.—Imbricated. Petaloids in the center: none to three; small.

*Petaloids*.—Length: 1/8–3/4 inch. Width: 3/4–15/16 inch. Surface texture: Smooth and velvety. Shape: Irregular; half-moon to heart-shaped. Upper Surface: Red Group 45A. Lower Surface: Red Group 46A to 46B often with a White Group 155B streak. Margin: Smooth with occasional notching.

*Persistence*.—Petals drop off cleanly before drying.

*Lastingness*.—On the plant: Long (about eight to nine days). As a cut flower: Not tested.

Reproductive parts:

*Stamens*.—Length: 3/16 inch.

*Anthers*.—Size: Medium. Length: 1/32 inch. Quantity: Many (55–60). Color: Yellow Group 13C. Arrangement: Regular around styles.

*Filaments*.—Color: Orange-Red Group 32A. Length: 1/8 inch.

*Pollen*.—Color: Between Yellow-Orange Group 22A and Yellow-Orange Group 22B.

*Pistils*.—Quantity: 15–20.

*Styles*.—Color: Red Group 46A.

*Stigmas*.—Color: Greyed-Yellow Group 160D.

*Seed hips*.—Size: 1/2 to 3/4 inches in diameter. Color: Near Yellow-Green Group 144B when mature.

*Seeds*.—Shape: Spherical. Size: 5/16 diameter. Surface texture: Smooth. Color: Yellow-Orange Group 22D.

Plant:

*Form*.—Bush.

*Growth*.—Vigorous; dwarf; upright; compact. At maturity, height is 20 to 28 inches, width is 20 to 28 inches.

Foliage: Number of leaflets on normal mid-stem leaves: Five; occasionally seven.

*Size*.—3 1/2 to 3 3/4 inches long×1 1/2 to 2 1/8 inches wide.

*Quantity*.—Abundant.

*Color*.—New foliage: Upper Surface: Near Yellow-Green Group 152C, overlaid with Greyed-Orange Group 178A. Lower surface: Near Greyed-Red Group 178A. Old foliage: Upper surface: Near Green Group 137A. Lower surface: Near Yellow-Green Group 147B.

Leaflets:

*Shape*.—Pointed oval.

*Texture*.—Glossy; smooth.

*Edge*.—Serrated.

*Serration*. —Mostly single; small.

*Petiole rachis*.—Color: Near Greyed-Purple Group 185A.

*Petiole underside*.—Smooth; with prickles; near Yellow-Green Group 146D.

*Stipules*.—Medium (about 5/8 inch long), serrated. Surface texture: Smooth. Color: Lower surface: Yellow-Green Group 144B. Upper surface: Yellow-Green Group 144A, with an overlay of Greyed-Red Group 181B.

*Disease resistance*.—Resistant to mildew and rust under normal growing conditions.

*Pest resistance*.—Not tested.

Wood:

*New wood*.—Color: Yellow-Green Group 144A with tints of Greyed-Red Group 178A. Bark: Smooth.

*Old wood*.—Color: Green Group 137C. Bark: Smooth.

Prickles:

*Quantity*.—On main canes from base: Ordinary. On laterals from main canes: Ordinary.

*Form*.—Short (about 1/4 inch); angled slightly downward.

*Color when young*.—Near Greyed-Purple Group 184A.

*Color when mature*.—Between Greyed-Orange Group 165A and Greyed-Orange Group 165B.

Small prickles:

*Quantity*.—On main stalks: None. On laterals: None.

*Hardiness*.—Hardy to Zone 5.

I claim:

1. A new and distinct variety of rose plant of the miniature class, substantially as herein shown and described, characterized particularly by its bright red, abundant flowers that darken in color as they age; dwarf, compact growth habit; dark green, glossy, abundant foliage; fast repeat bloom cycle; and resistance to powdery mildew.

* * * * *

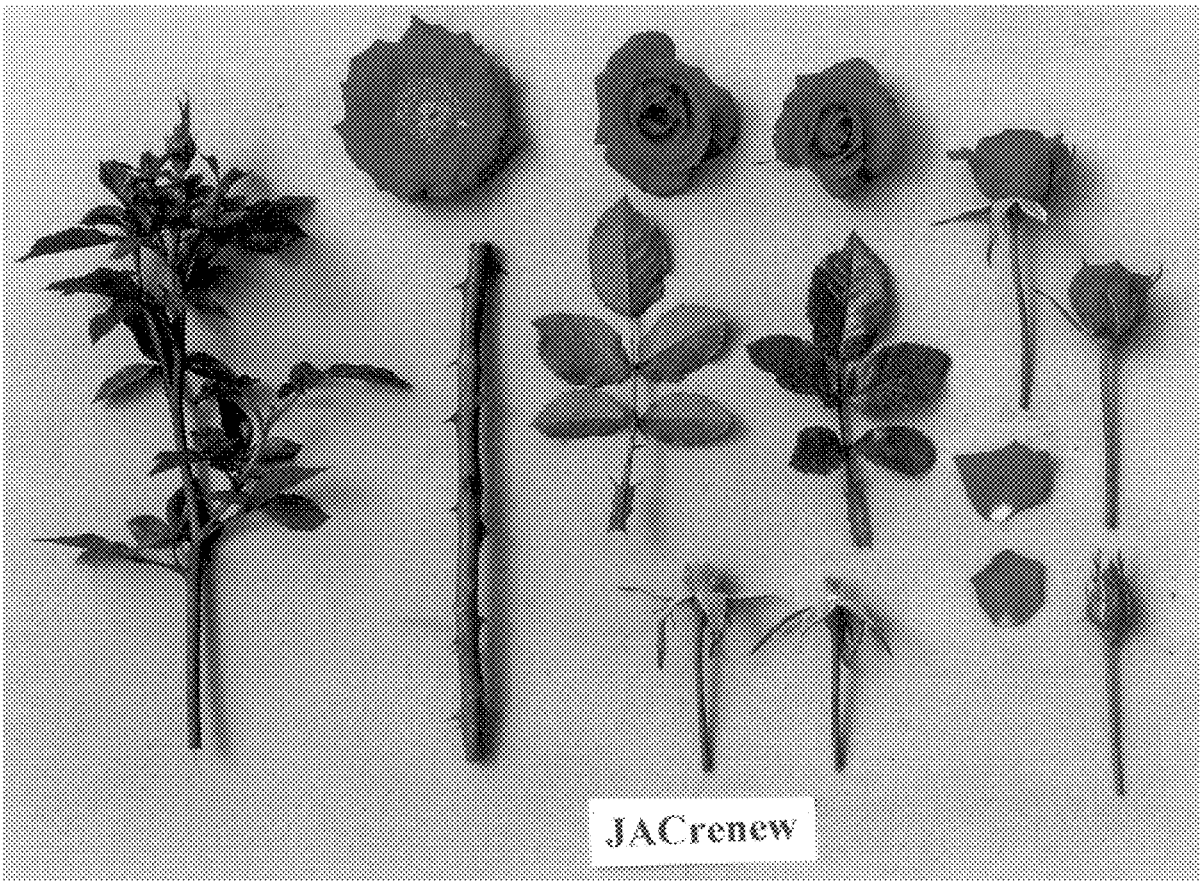
JACrenew